United States Patent [19]

Shimomura et al.

[11] Patent Number: 5,123,904
[45] Date of Patent: Jun. 23, 1992

[54] SURGICAL RESECTING INSTRUMENT

[75] Inventors: Koji Shimomura; Shozo Shibuya, both of Hachioji, Japan

[73] Assignee: Olympus Optical Co., Ltd., Tokyo, Japan

[21] Appl. No.: 633,194

[22] Filed: Dec. 31, 1990

Related U.S. Application Data

[63] Continuation of Ser. No. 316,886, Feb. 28, 1990, abandoned.

[30] Foreign Application Priority Data

Apr. 28, 1988 [JP] Japan .................................. 63-57466
Apr. 28, 1988 [JP] Japan .................................. 63-57467
Aug. 9, 1988 [JP] Japan .................................. 63-199198
Aug. 29, 1988 [JP] Japan .................................. 63-113955

[51] Int. Cl.⁵ ............................................. A61B 17/32
[52] U.S. Cl. ....................................... 604/22; 606/170
[58] Field of Search ............... 606/170, 171, 180, 159; 604/22

[56] References Cited

U.S. PATENT DOCUMENTS

| | | | |
|---|---|---|---|
| 3,732,858 | 5/1973 | Banko | 606/170 X |
| 3,882,872 | 5/1975 | Douvas et al. | 606/170 X |
| 4,274,414 | 6/1981 | Johnson et al. | 606/170 |
| 4,517,977 | 5/1985 | Frost | 606/170 |
| 4,649,919 | 3/1987 | Thimsen et al. | |
| 4,770,174 | 9/1988 | Luckman et al. | 606/180 |

FOREIGN PATENT DOCUMENTS 8707238.6 9/1987 Fed. Rep. of Germany .

Primary Examiner—Michael H. Thaler
Attorney, Agent, or Firm—Armstrong, Nikaido, Marmelstein, Kubovcik, & Murray

[57] ABSTRACT

A surgical resecting instrument whereby a cartilage, joint bump or tumor within a body cavity such as a joint cavity, for example, of a knee is resected from outside the body cavity without incising it and is discharged out of the body cavity has a body part providing a rotary driving connection and an insertable part to be inserted into a tissue within a living body attached to and extending from a front end part of the body part. The insertable part comprises a tubular outer tube opened in the tip part and forming an outer shell of the insertable part and an inner tube provided within the outer tube and rotated and driven by the rotary driving connection. An outer tubular blade is provided in the tip part of the outer tube. The tip of the outer blade is open and has a slot extending from the tip in a peripheral wall and forming a blade part at an edge of the slot. An inner blade for shearing a living body tissue together with the outer blade part is provided in the tip part of the inner tube within the outer blade. The inner blade has a shearing blade part formed so that the angle formed with the outer blade part at the beginning of a shearing action will be larger than the angle formed with the blade part as the shearing action continues.

7 Claims, 16 Drawing Sheets

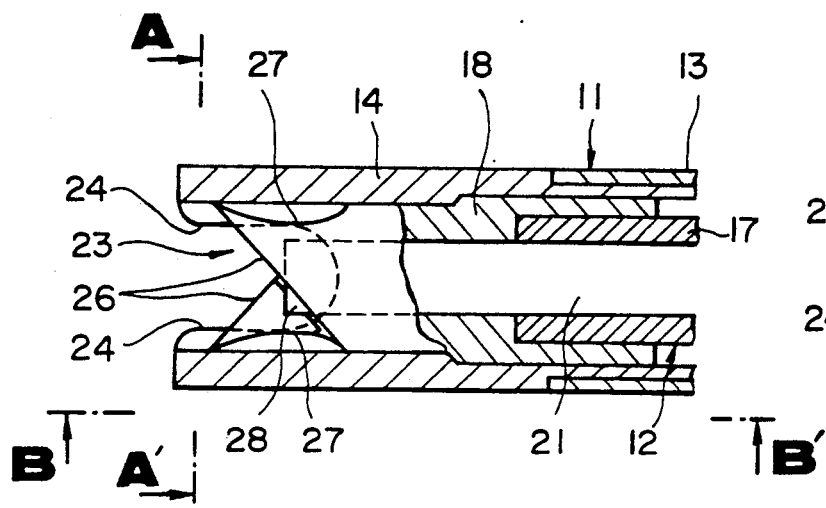
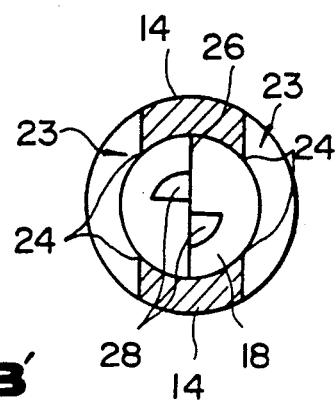
FIG. 4　　FIG. 5
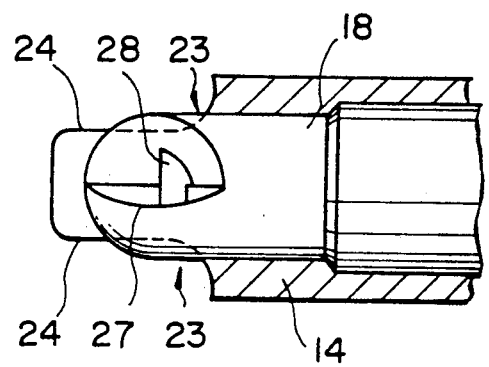
FIG. 6
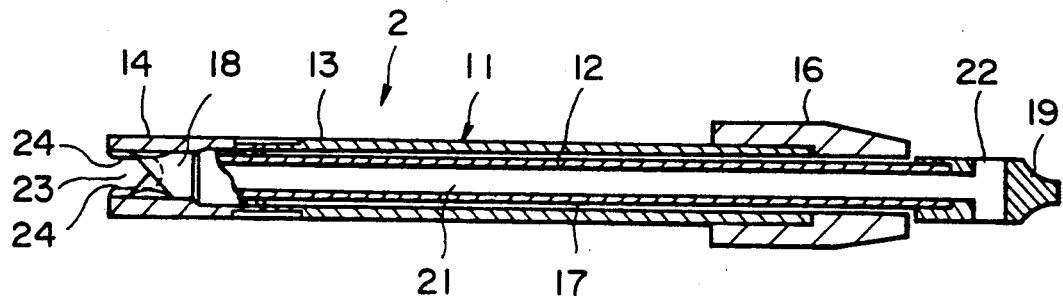
FIG. 7

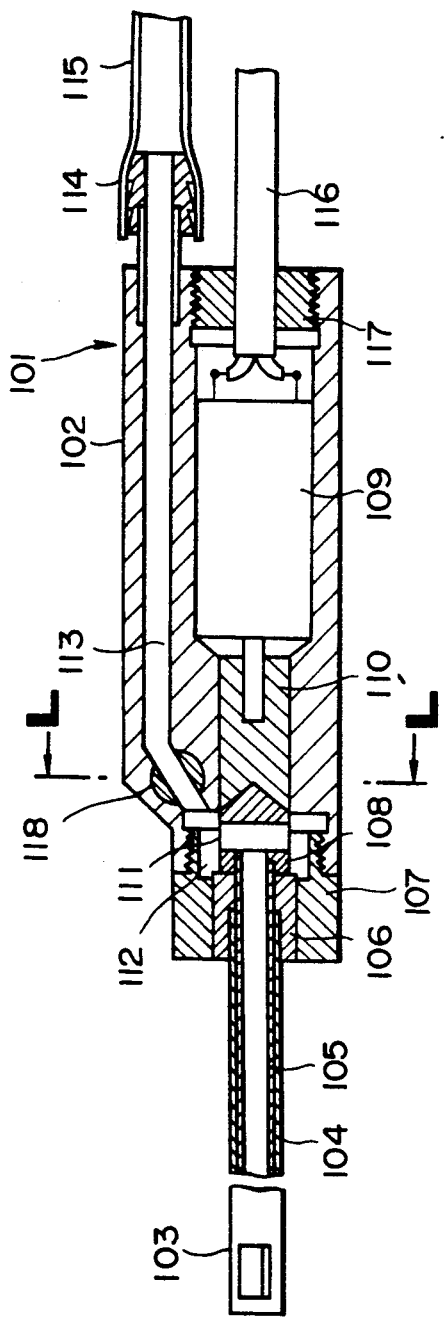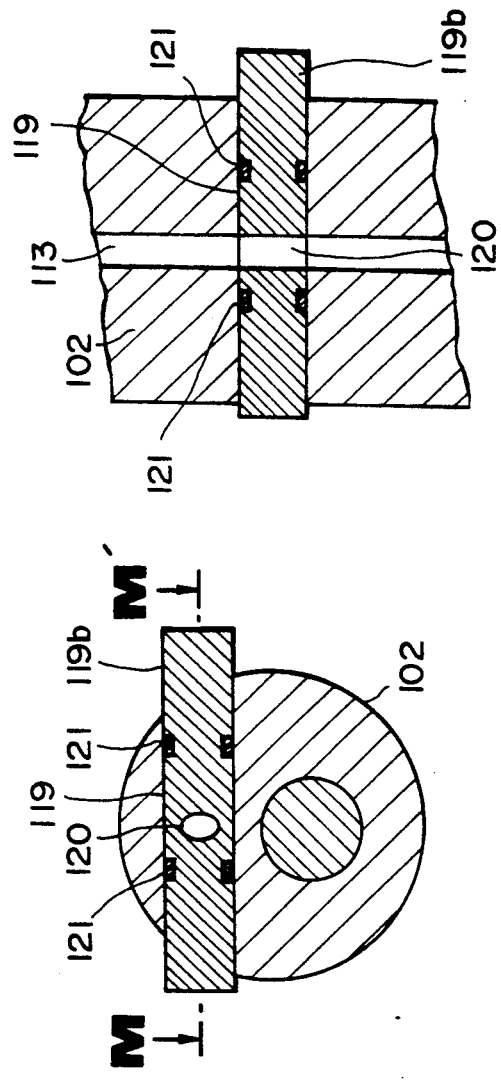

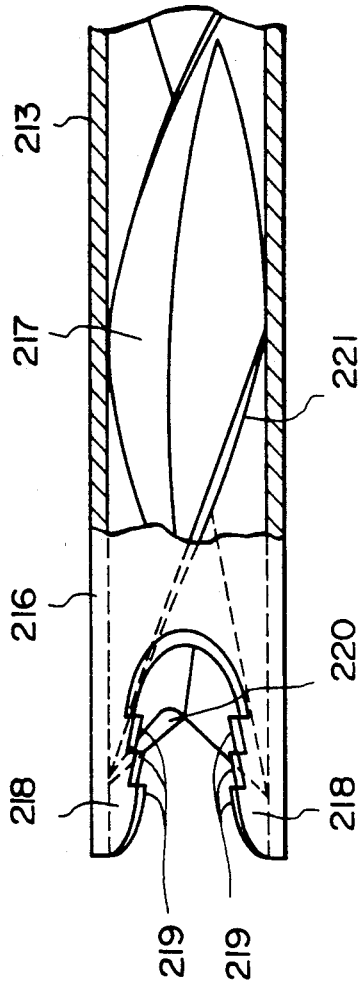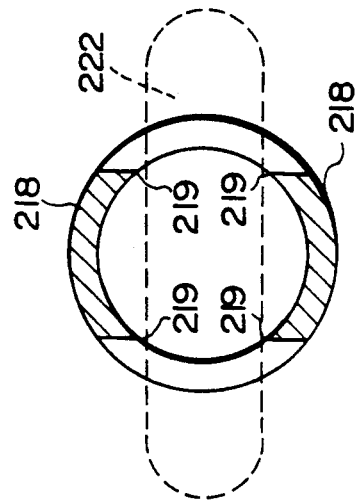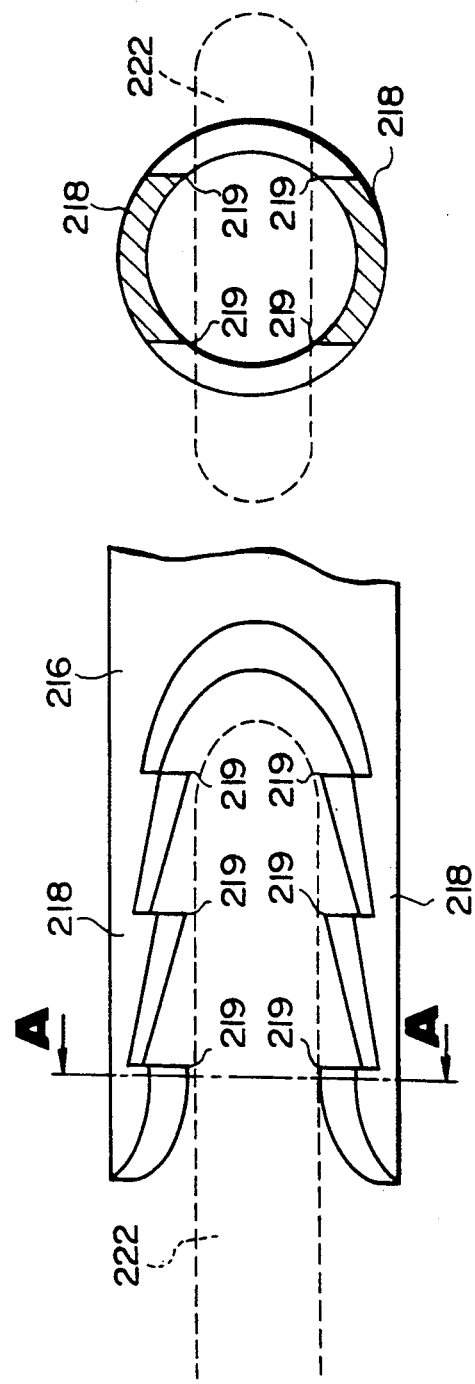

SURGICAL RESECTING INSTRUMENT

This application is a continuation of application Ser. No. 316,886 filed Feb. 28, 1989 now abandoned.

FIELD AND BACKGROUND OF THE INVENTION

This invention relates to a surgical resecting instrument whereby a cartilage (joint semicircle or joint cartilage), joint bump or tumor within such body cavity as a joint cavity, for example, of a knee is resected from outside the body cavity without incising it and is discharged out of the body cavity.

Conventionally, a joint has been operated on mostly by an incising method (open surgery). For example, in a general operation on a joint, a tumor on a knee skeleton is resected or a broken cartilage or bone is resected from a knee joint. Such operation has required a comparatively large incision. Therefore, there have been such defects that an external hurt will be produced by the incision, a pain and motion limitation will follow and much time will be required until the hurt is perfectly cured.

Therefore, there is recently suggested a surgical resecting instrument whereby, under the observation with a joint scope (endoscope), without incising a joint, a small stinging hole is formed in the joint and an insertable part is inserted into this stinging hole to operate on the joint. For example, in the publication of U.S. Pat No. 4,649,919, there is disclosed a surgical resecting instrument having an insertable part in which a rigid linearly extending inner tube provided at the tip with a cutting part is inserted through a rigid linearly extending outer tube. With this surgical resecting instrument, while a tissue is being bored with the tip of the inner tube, the tissue is shorn with a side opening near the tip. A blade for resecting this tissue is formed of an outer blade provided in the axial direction in a cylindrical outer tube and an inner blade (helcal cutter blade) rotatably inserted in the outer blade, having a fish tail-like cutting blade at the tip and provided on the side with a helical cutting blade.

Also, in German Utility Model No.8707238, there is disclosed a surgical resecting instrument wherein an inner blade having a helical blade at the tip is formed to be hollow and a sucking device is connected to this hollow part.

Now, in the above mentioned prior art, as the cutting blade on the side of the inner blade is formed to be helical, the shearing angle $\theta$ in the case that the inner blade shears the tissue in cooperation with the opening of the outer blade has been constant as in FIG. 1.

Here, the shearing power P (in kg) is represented by the following formula:

$$P = t^2 \tau / (2 \tan \theta)$$

t : Thickness (in mm) of the shorn tissue.

$\tau$: Shearing resistance (in kg/mm$^2$).

From the above formula, in case t and $\tau$ are constant, if the shearing angle $\theta$ is constant, the shearing power P will not fluctuate and such smooth shearing as is shown by the broken line in FIG. 2 will be made. However, in fact, as shown by the solid line in FIG. 2, the shearing power increases quickly at the beginning of the shearing stroke and then decreases to be constant in the course. When the shearing power thus quickly increases, the rotating speed will vary, the cutting efficiency will drop, a repeated stress will be applied to the cutting blade and therefore the blade will be likely to be fatigued and broken and will not be safe. Further, there is a problem that, when the side of the inner blade is formed to be a helical cutting blade, it will be difficult to work and expensive.

OBJECT AND SUMMARY OF THE INVENTION

An object of the present invention is to provide a surgical resecting instrument whereby, in the case of shearing a living body tissue, the shearing power will not increase at the beginning of the shearing and the blade can be prevented from the cutting efficiency reduction, fatigue and break and is easy to work.

The surgical resecting instrument of the present invention is provided with an outer blade having a blade part and an inner blade having a shearing blade part and is formed so that the shearing angle formed by the outer blade and shearing blade part may vary with the shearing process In the present invention, the shearing angle in the course the shearing is made smaller than the shearing angle at the beginning of the shearing.

BRIEF DDESCRIPTION OF THE DRAWINGS

FIGS. 1 and 2 relate to prior art examples.

FIGS. 3 to 13 relate to the first embodiment of the present invention.

Figure 3:
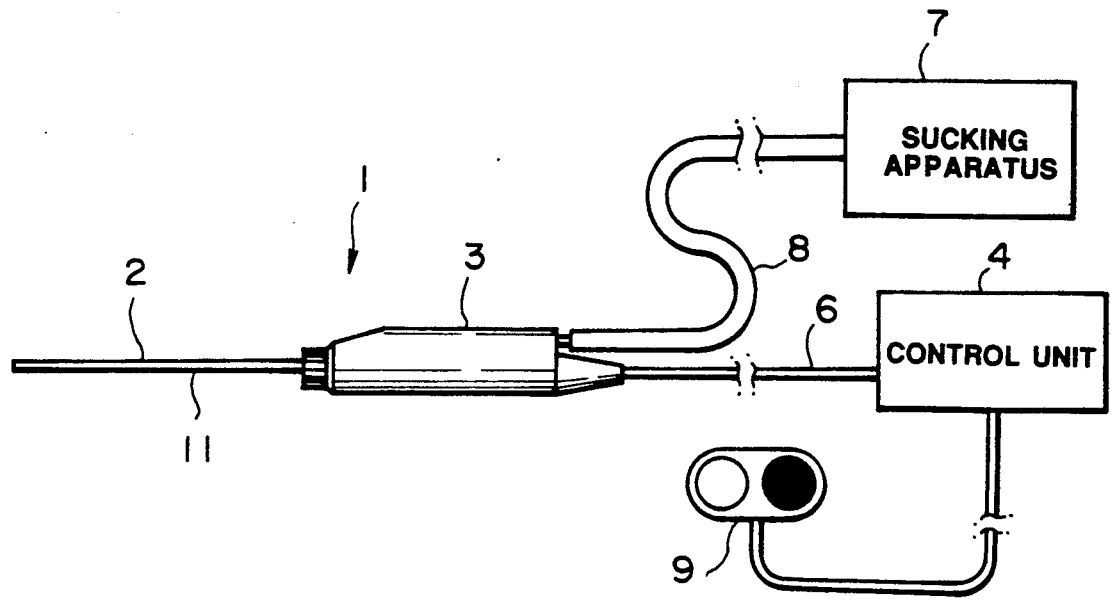

FIG. 3 is an explanatory view showing the formation of a surgical resecting instrument.

FIG. 4 is a sectioned view of a tip part of a surgical resecting instrument.

FIG. 5 is a sectioned view in the direction A-A' in FIG. 4.

FIG. 6 is a sectioned view in the direction B-B' in FIG. 4.

FIG. 7 is a sectioned view of an inner tube inserted through an outer tube.

Figure 8:
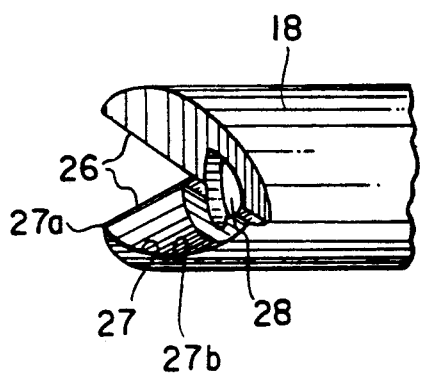

FIG. 8 is a perspective view of an inner blade.

Figure 9:
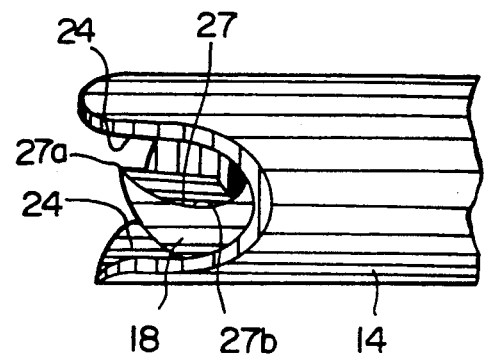

FIG. 9 is a perspective view showing the state of an outer blade and an inner blade inserted through the outer blade.

Figure 10:
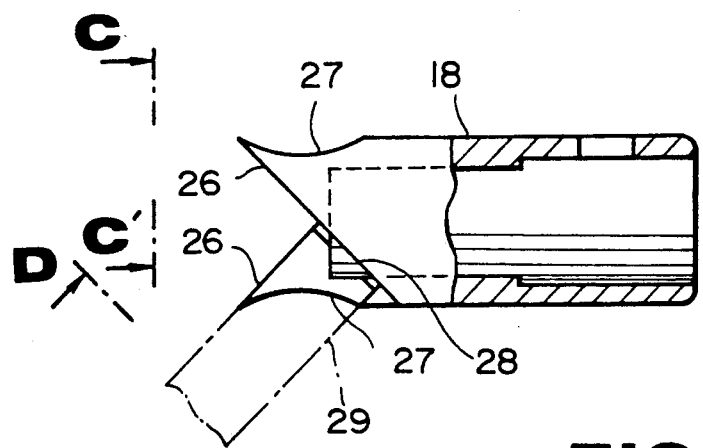

FIG. 10 is an elevation of the inner blade.

Figure 11:
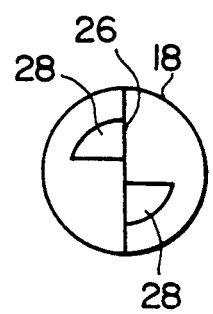

FIG. 11 is a view as seen in the arrow direction C—C' in FIG. 10.

Figure 12:
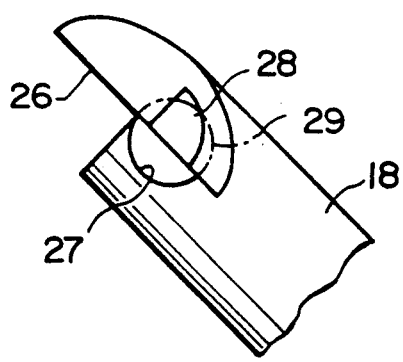

FIG. 12 is a view as seen in the arrow direction D-D' in FIG. 10.

Figure 13:
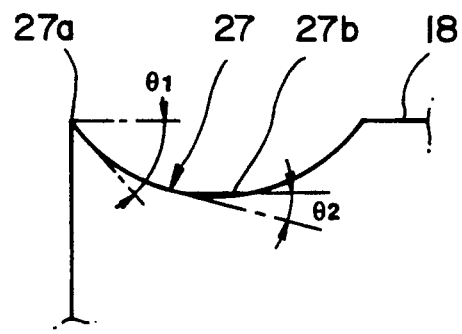

FIG. 13 is a magnified view of the inner blade.

FIGS. 14 to 18 relate to the second embodiment of the present invention.

Figure 14:
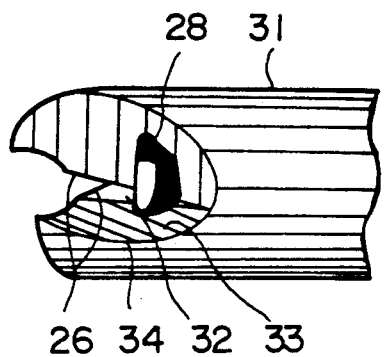

FIG. 14 is a perspective view of an inner blade.

Figure 15:
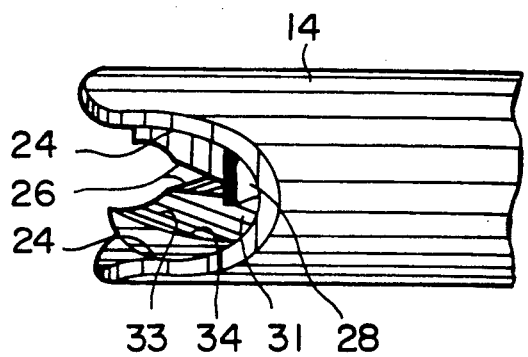

FIG. 15 is a perspective showing the state of an outer blade and an inner blade inserted through the outer blade.

Figure 16:
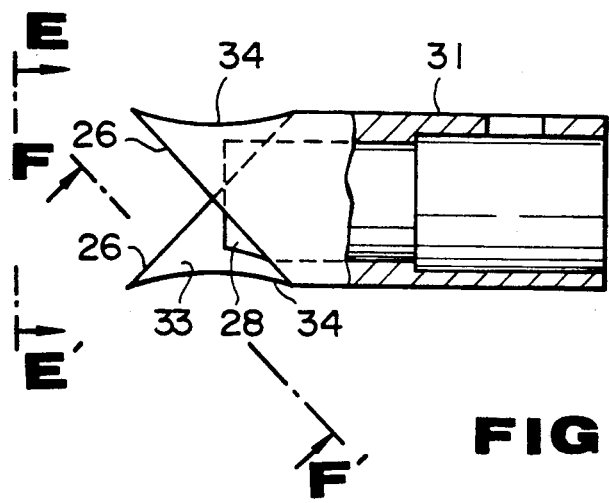

FIG. 16 is an elevation of the inner blade.

Figure 17:
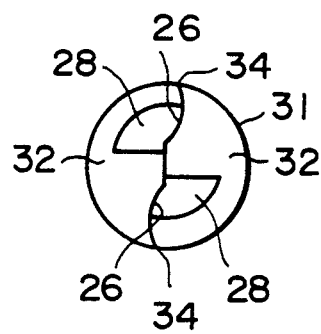

FIG. 17 is a view as seen in the arrow direction E—E' in FIG. 16.

Figure 18:
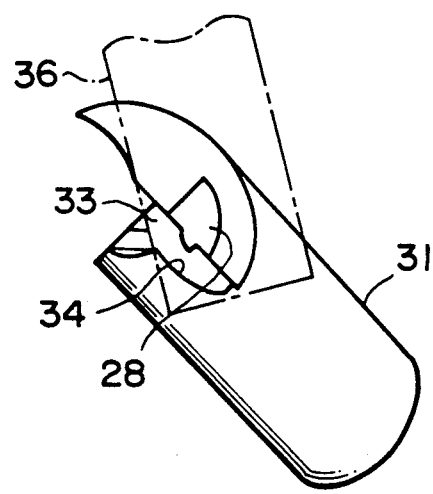

FIG. 18 is a view as seen in the arrow direction F—F' in FIG. 16.

FIGS. 19 to 24 relate to the third embodiment of the present invention.

Figure 19:
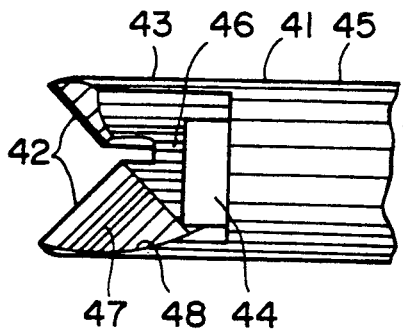

FIG. 19 is a perspective view of an inner blade.

Figure 20:
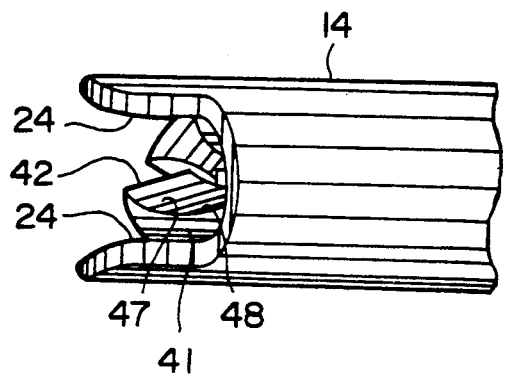

FIG. 20 is a perspective view showing the state of an outer blade and an inner blade inserted through the outer blade.

Figure 21:
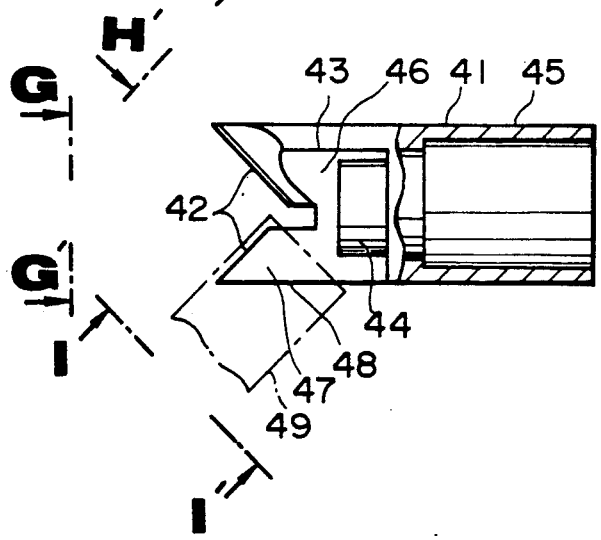

FIG. 21 is an elevation of the inner blade.

Figure 22:
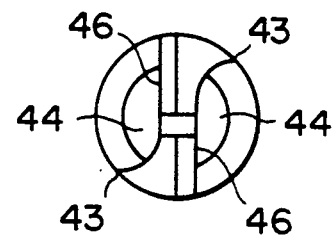

FIG. 22 is a view as seen in the arrow direction G—G' in FIG. 21.

Figure 23:
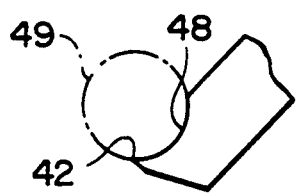

FIG. 23 is a view as seen in the arrow direction H—H' in FIG. 21.

Figure 24:
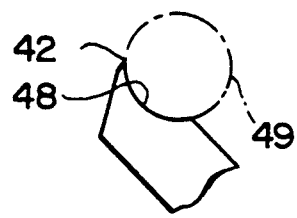

FIG. 24 is a view as seen in the arrow direction I—I' in FIG. 21.

FIGS. 25 to 28 relalte to the fourth embodiment of the present invention.

Figure 25:
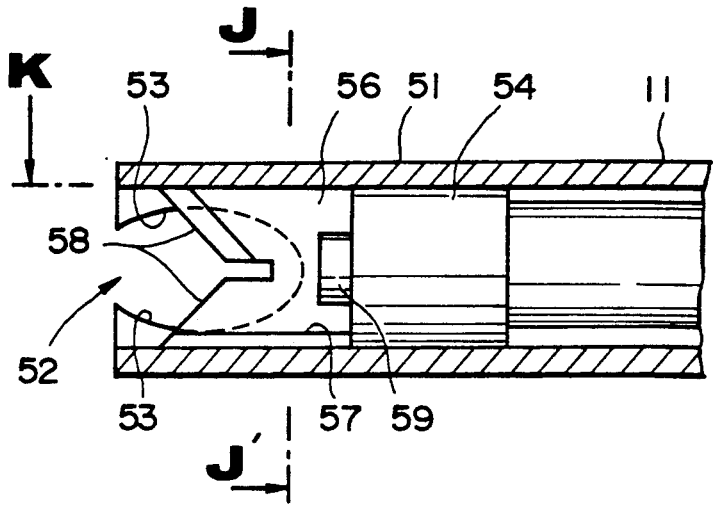

FIG. 25 is a sectioned view of the tip side of an insertable part.

Figure 26:
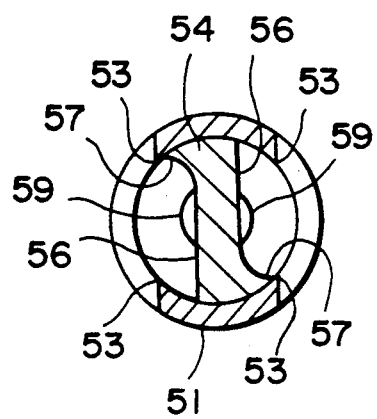

FIG. 26 is a sectioned view in the direction J—J' in FIG. 25.

Figure 27:
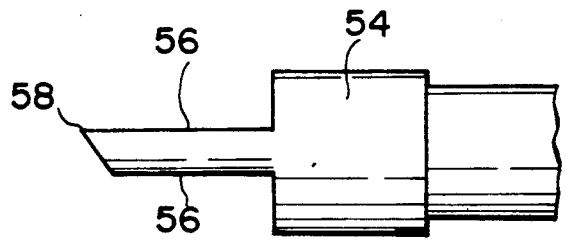

FIG. 27 is a view as seen in the arrow direction K in FIG. 25.

Figure 28:
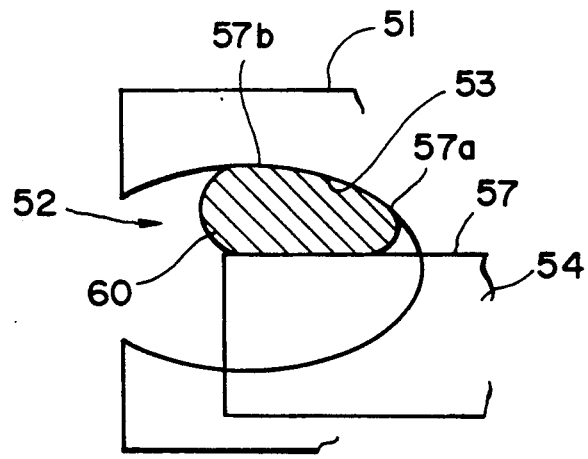

FIG. 28 is an explanatory view of a shearing cutting blade and the shearing state with the cutting blade.

FIG. 29 is a vertically sectioned view of a surgical resecting instrument.

FIG. 30(a) is a sectioned view on line L—L' in FIG. 29.

FIG. 30(b) is a sectioned view on line M-M' in FIG. 30(a).

Figure 31:
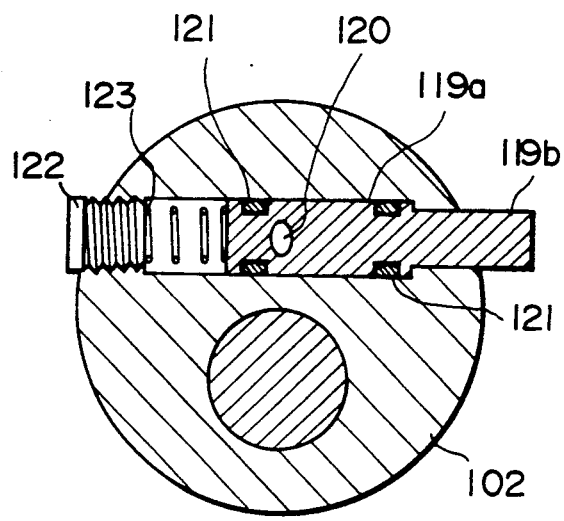

FIG. 31 is a sectioned view showing a suction volume adjusting valve having a spring.

Figure 32:
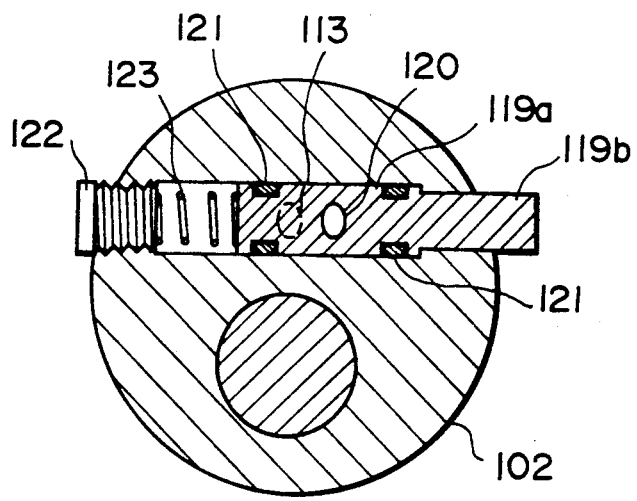

FIG. 32 is a sectioned view showing a suction volume adjusting valve opend by pressing the spring.

Figure 33:
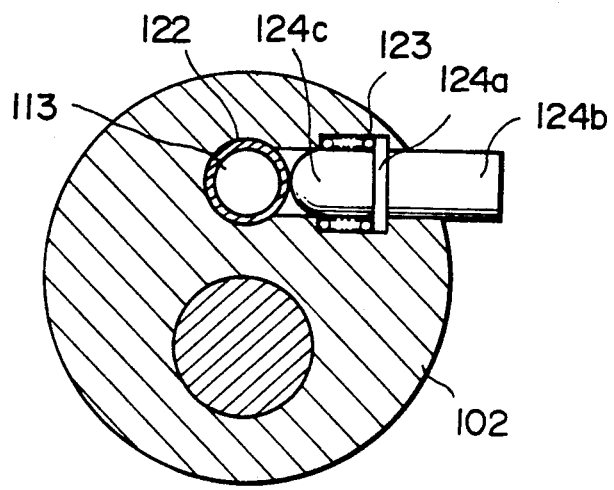

FIG. 33 is a sectioned view showing a suction volume adjusting valve having a suction path formed of an elastic tube.

Figure 34:
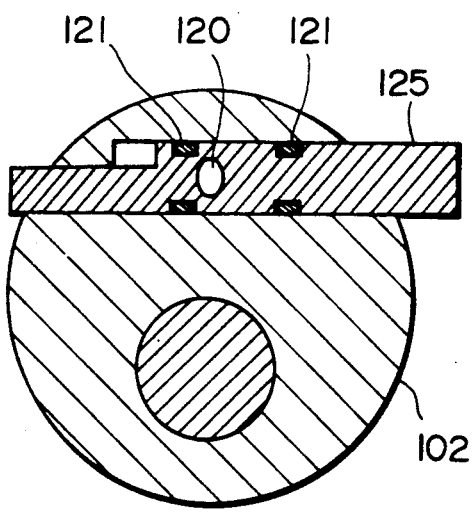

FIG. 34 is a sectioned view showing a suction volume adjusting valve having the shape of the piston varied.

FIG. 35 is an explanatory view showing a suction volume adjusting valve in operation.

Figure 36:
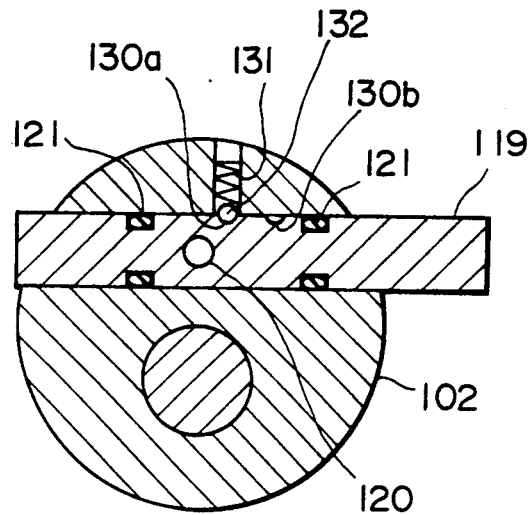

FIG. 36 is a sectioned view showing a suction volume adjusting valve having a clicking mechanism.

Figure 37:
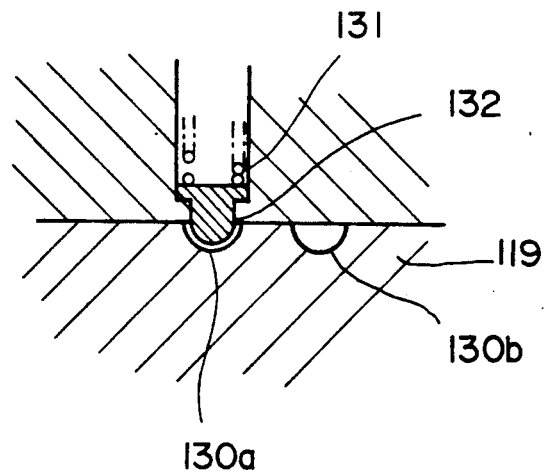

FIG. 37 is a magnified view of the clicking mechanism in FIG. 36.

Figure 38:
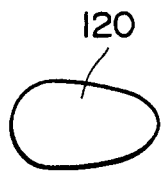
Figure 38:
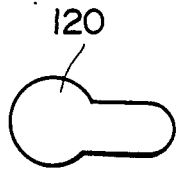
Figure 38:
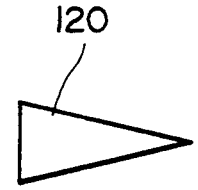

FIG. 38 is an explanatory view showing the shape of another suction volume adjusting hole.

FIGS. 39 to 44 relate to the explanation of an insertable part having a suction path washing hole.

Figure 39:
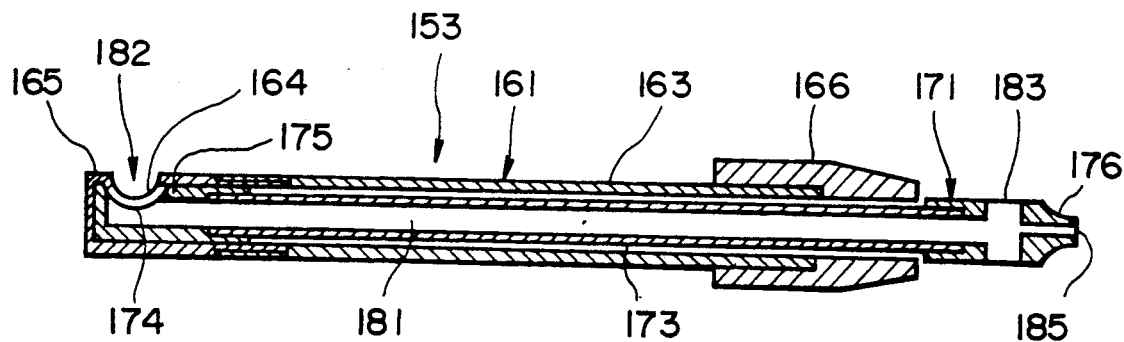

FIG. 39 is a sectioned view of the insertable part.

Figure 40:
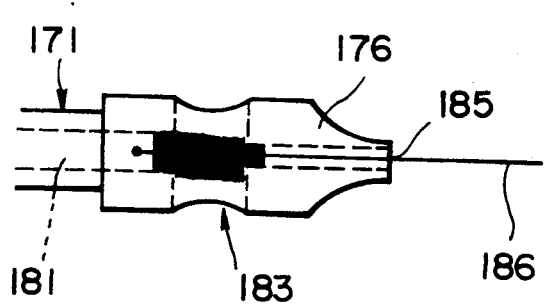

FIG. 40 is an explanatory view showing a washing brush as inserted through the washing hole.

Figure 41:
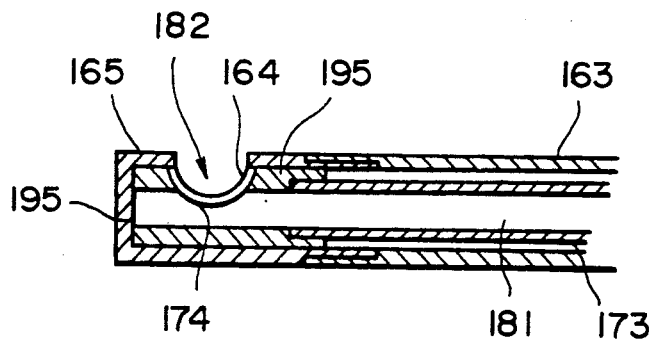

FIG. 41 is a sectioned view of the tip side of another insertable part.

Figure 42:
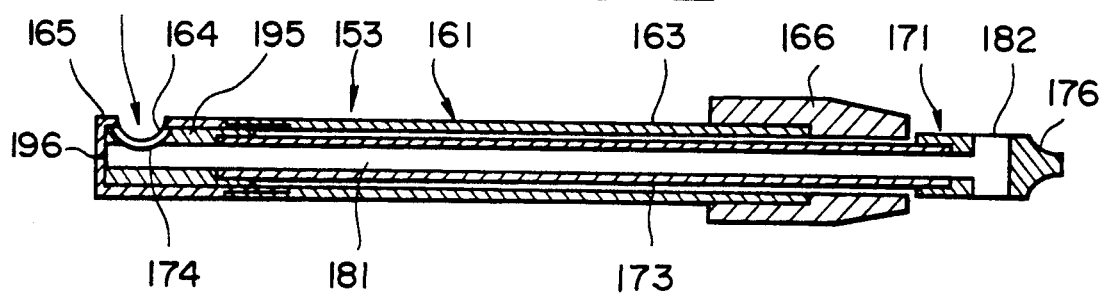

FIG. 42 is a sectioned view of an inner tube having a washing hole on the tip side.

Figure 43:
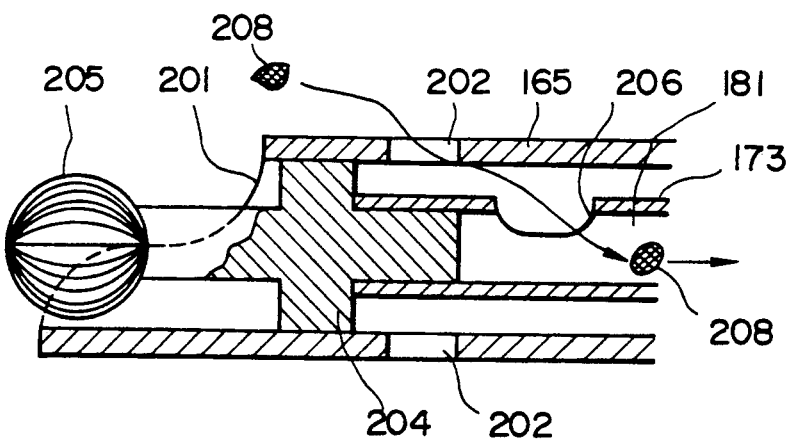

FIG. 43 is a sectioned view of an inner tube having a spherical cutting blade.

Figure 44:
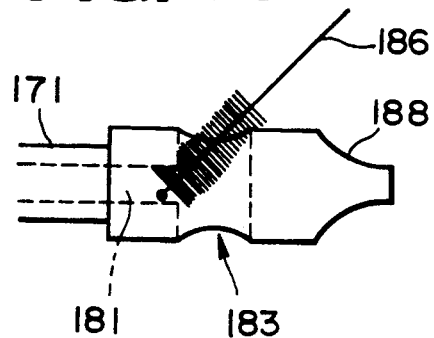

FIG. 44 is an explanatory view of washing a suction path.

FIGS. 45 to 48 relate to a surgical resecting instrument having a holding member holding a living body tissue.

FIG. 45 is a side view of the tip side of an insertable part.

FIG. 46 is an explanatory view of taking a semicircular plate into the tip of the insertable part.

Figure 47A:
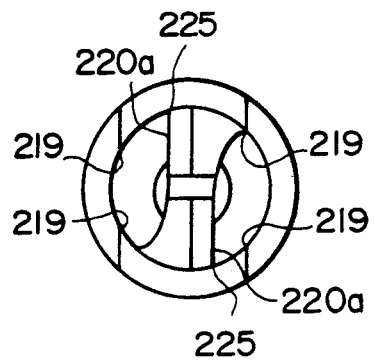
Figure 47B:
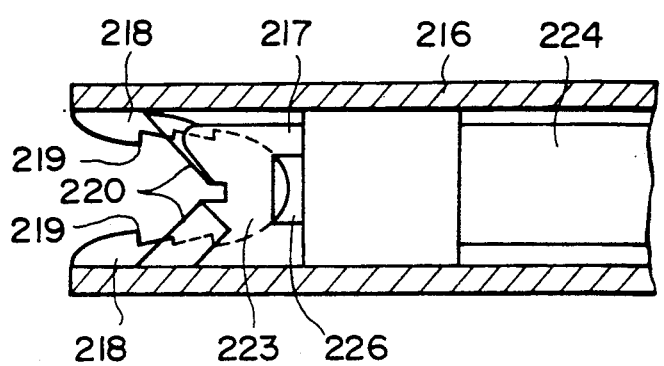

FIG. 47 is an explanatory view of the tip of another insertable part having serrated cutting blades.

Figure 48A:
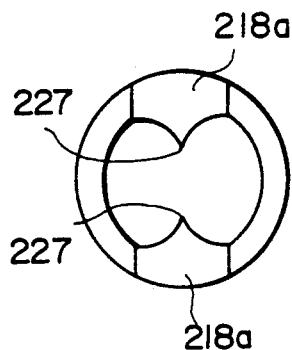
Figure 48B:
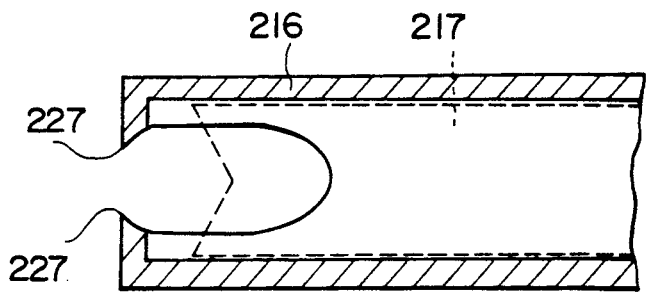
Figure 48C:
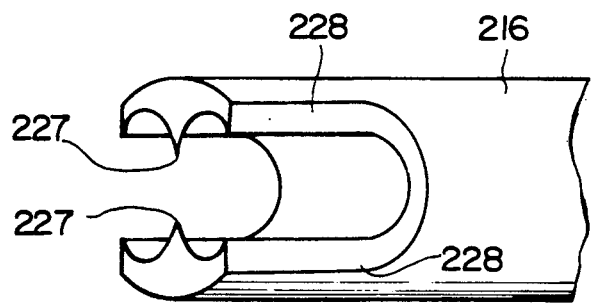

FIG. 48 is an explanatory view of the tip of an insertable part having a projection.

DETAILED DESCRIPTION OF PREFERRED EMBODIMENTS OF THE INVENTION

FIGS. 3 to 13 show the first embodiment of the present invention.

In FIG. 3, a surgical resecting instrument 1 is provided with a rigid linearly formed insertable part 2 and a body part 3 provided in the rear of this insertable part. A power source cord 6 is connected to the rear end part of the body part 3. Through this power source cord 6, an electric power is fed to such driving apparatus as, for example, a motor provided within the body part 3 from a control unit 4. A foot switch 9 is connected to this control unit 4 so that the operator operating the surgical resecting instrument 1 may control the drive of the motor with the foot. Further, a sucking apparatus 7 discharging broken pieces of a resected living body tissue out of the body is connected to the rear end surface of the body part 3 through a tube 8.

As in FIG. 7, the above mentioned insertable part 2 is provided with a rigid linearly formed outer tube 11 and an inner tube 12 inserted through this outer tube 11. This outer tube 11 has a tube member 13 opening at both ends. This tube member 13 is provided at one end with a substantially cylindrical outer blade 14 made of stainless steel and has at the other end a cylindrical connecting member 16 removably connected with the front part of the above mentioned body part fixed with a solder or the like.

The inner tube 12 has a tube member 17 of an outside diameter slightly smaller than the inside diameter of the outer tube 11. This tube member 17 is opened at both ends and is externally fitted in the end part on the outer blade 14 side with an inner blade 18 made of stainless steel. The outside diameter of this inner blade 18 is somewhat smaller than the inside diameter of the outer blade 14 so that the inner blade 18 may be rotatable with respect to the outer blade 14. The tube member 17 is externally fitted in the other end part with a substantially cylindrical sleeve 19. A communicating hole 22 communicating with a suction path 21 provided within the tube member 17 is provided through the peripheral wall of this sleeve 19. Further, this sleeve 19 is connected to a motor provided within the body part 3 and can transmit a torque to the inner tube 12.

In FIGS. 4 and 6, the outer blade 14 opens forward and is provided on the peripheral wall with a pair of incised parts 23 incised and forming slots extending from the front end part and cutting blades 24 are formed in the edge parts positioned in the lengthwise direction of these incised parts 23 i.e., slots 23. The above mentioned inner blade 18 is positioned within this outer blade 14. Two sharp boring cutting blades 26 for boring cutting are formed to be V-shaped in the tip part of this inner blade 18. This inner blade 18 has on the peripheral wall shearing cutting blades 27 as arcuately formed sharp shearing cutting parts and is provided on the front end surface with a window 28 communicating with the suction path 21 of the tube member 17. In FIGS. 10 and 12, such shearing cutting blade 27 is formed by being cut from the oblique front with a cylindrical cutting tool 29 as shown by phantom (dot-dash) lines.

The blade 27 of the tip part of the inner blade 18 as shown in FIG. 8 appears different from the orientation of the blade 27 as shown by FIGS. 4 and 10 because the inner blade 18 is shown as being rotated to a different position in FIG. 8.

The operation of the surgical resecting instrument 1 formed as mentioned above shall be explained.

For example, in the case of resecting the semicircular plate part of a knee joint, the semicircular plate is taken in between a pair of the incised parts 23 and, while being bored and cut with the boring cutting blade 26, the semicircular plate is shorn on the side surface with the cutting blade 24 and shearing cutting blade 27 to resect a living body tissue. In FIGS. 5 and 9, the shearing stroke shall be explained. At the beginning of the shearing, the cutting will be made by the cutting blade 24 and the tip part 27a of the shearing cutting blade 27. When the cutting progresses, the cutting will be made by the cutting blade 24 and the rear part 27b of the shearing cutting blade 27. Further, the explanation shall be made by using FIG. 13. As the shearing cutting blade 27 is formed to be arcuate, as the shearing stroke progresses, the angle formed by the cutting blade 24 and shearing cutting blade 27, that is, the shearing angle $\theta$ will become gradually smaller and, when the shearing angle formed by the cutting blade 24 and the tip part 27a of the shearing cutting blade 27 at the beginning of the shearing is represented by $\theta_1$ and the shearing angle in the shearing cource is represented by $\theta_2$, the relation of $\theta_1 > \theta_2$ will be made.

Figure 1:
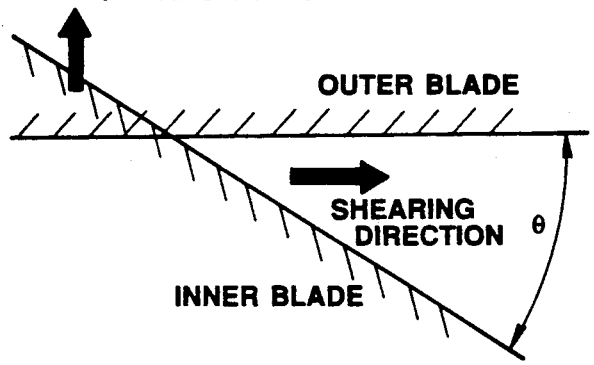
FIG. 1 is an explanatory view of a shearing angle.
Figure 2:
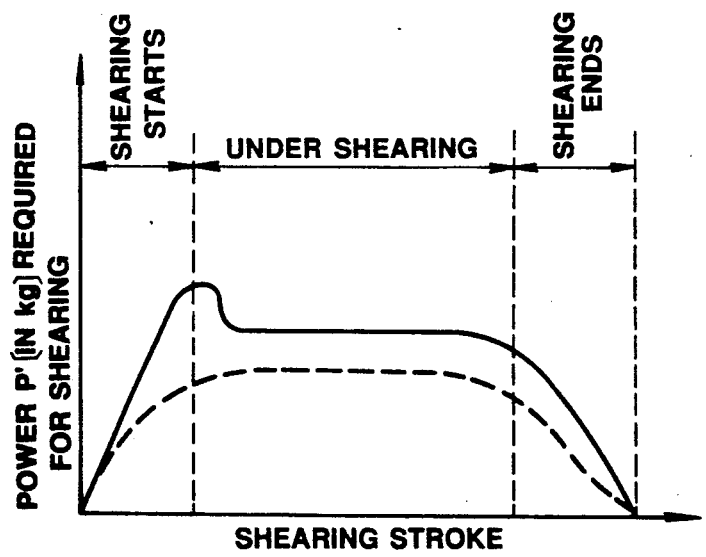
FIG. 2 is an explanatory view of a shearing power varying with a shearing stroke.

Here, if the shearing angle $\theta$ is constant, at the beginning of the shearing, as shown in FIG. 2, the shearing power P will become larger but, as the shearing angle is varied as mentioned above and is made large at the beginning of the shearing, by the formula $P = t^2 \tau / (2 \tan \theta)$, the shearing power P will not become larger. Therefor, at the beginning of the shearing, the shearing power P will be able to be prevented from quickly increasing, the rotating speed will not largely vary and the cutting efficiency will improve to be higher than ever. Further, as the repeated load applied to the cutting blade becomes smaller, the blade tip will be hardly fatigued or broken.

FIGS. 14 to 18 show the second embodiment of the present invention.

The same as in the first embodiment, the inner blade 31 of this embodiment has a boring cutting blade 26 formed to be V-shaped in the tip part. In the plane part 32 in the axial direction forming this boring cutting blade 26, the same arcuate part 33 is formed from the cutting blade 26 to the peripheral wall of the inner blade 31. A shearing cutting blade 34 as a shearing cutting part is formed of this arcuate part 33 and the peripheral wall. A window 28 communicating with the suction path 21 of the tube member 17 is provided in the front end part of the inner blade 31.

Further in FIGS. 16 to 18, the shearing cutting blade 34 is formed by being cut so as to intersect with the lengthwise direction center of the inner blade 31 in the oblique front by a cylindrical cutting tool 36.

In this embodiment, too, the same as in the first embodiment, a shearing cutting blade 34 is formed to be arcuate and therefore the angle formed with the cutting blade 24 formed in the outer blade 14, that is, the shearing angle $\theta$ will vary with the shearing stroke and the shearing power at the beginning of the shearing will not quickly increase.

The other formations and operations are the same as in the first embodiment.

FIGS. 19 to 24 show the third embodiment of the present invention.

The tip surface of an inner blade 42 of this embodiment is incised to be in the form of V to form boring cutting blades 42. Further, a part of the tip peripheral wall 45 is cut off to form opposed plane parts 46. A cutting blade 43 is formed in one edge part extending in the lengthwise direction of these plane parts 46 and peripheral wall 45. A window 44 communicating with the suction path 21 is provided in the plane part 46. An arcuate part 47 is formed on the plane part 46 on the opposite surface side of the cutting blade 43. An arcuate shearing cutting blade 48 as a shearing blade part is formed in the edge part of this arcuate part 47 and peripheral wall 45.

Further, in FIGS. 21 to 24, the shearing cutting blade 48 is formed by being cut to be cylindrical from the oblique front with a cutting tool 49.

In the case of this embodiment, as the shearing cutting blade 48 is formed to be arcuate the same as in the first embodiment, the shearing angle $\theta$ formed by the shearing cutting blade 48 and cutting blade 24 will be large at the beginning of the shearing. Therefore, the shearing power at the beginning of the shearing will not quickly increase.

FIGS. 25 to 28 show the fourth embodiment of the present invention.

In the above mentioned embodiment, the inner blade is made to have an angle but, in this embodiment, the shearing cutting blade of the inner blade is made linear and the cutting blade of the outer blade is made to have an angle.

A tubular outer blade 51 opens forward and is provided on the peripheral wall with a pair of incised parts 52 incised from the front end part. This incised part 52 is substantially elliptic, the major diameter of this ellipse coincides with the lengthwise direction of the outer tube 11 and the minor diameter of the ellipse is positioned on the body part 3 side from the tip part. A cutting blade 53 is formed in the edge part of this incised part 52.

An inner blade 54 is positioned within the outer blade 51. The peripheral wall on the tip side of this inner blade 54 is incised to form facing incised planes 56 as shown in FIG. 26. A shearing cutting blade 57 shearing together with the above mentioned cutting blade 53 is formed in one edge part positioned in the lengthwise direction of this incised plane 56. Further, boring cutting blades 58 are formed to be V-shaped on the tip surface of the inner blade 54. The tip part of this boring cutting blade 58 is positioned near the minor diameter of the above mentioned substantially elliptic cutting blade 53.

A window 59 communicating with a suction path is provided in the root part of the incised plane 56.

The other formations are the same as of the first embodiment.

The resection of a living body tissue shall be explained by using FIG. 28. The living body tissue 60 to be shorn with the cutting blade 53 and shearing cutting blade 57 is held by the incised parts 52. When the inner blade 54 is rotated and driven, resection will be started with the cutting blade 53 and shearing cutting blade 57. The position of this resection is a position of intersecting the cutting blade 53 and shearing cutting blade 57 with each other. With the progress of the resecting stroke, the shearing will move from the position 57a on the major diameter side to the position 57b on the minor diameter side. The shearing angle $\theta$ formed by this cutting blade 53 and shearing cutting blade 57 will be gradually smaller. If the shearing angle formed by the cutting blade 53 and shearing cutting blade 57 at the beginning of the shearing is represented by $\theta_1$ and the shearing angle in the course of the shearing is represented by $\theta_2$, $\theta_1 > \theta_2$. By thus enlarging the shearing angle $\theta_1$ at the beginning of the shearing, as described in the first embodiment, the shearing power P can be prevented from becoming larger.

The other operations and effects are the same as in the first embodiment.

By the way, in this embodiment, the cutting blade 53 is formed to be substantially elliptic but may be formed to be arcuate.

By the way, the shapes of the inner blade and outer blade are not limited to those in the above mentioned respective embodiments but may be any shapes in which the shearing angle formed by this shearing cutting blade and the cutting blade provided in the outer blade will reduce with the progress of the shearing from the beginning of the shearing.

Also, the material of the inner blade and outer blade need not be stainless steel but may be any of such materials which can be used as materials for blades as, for example, ceramics and tool steel.

By the way, in the surgical resecting instruments described in the above mentioned respective embodiments, the sucked and discharged amount of the tissue resected by the cutting blade as in FIGS. 29 to 38 may be adjusted.

As shown in FIG. 29, a surgical resecting instrument 101 comprises a body 102 and an insertable part 103 of a fine diameter connected to the front end of this body 102.

The above mentioned insertable part 103 has a cutting blade in the tip part. For example, this cutting blade comprises an outer blade 104 formed by providing an opening 103a by incising a part of the tip side of the above mentioned insertable part 103 and making the edge part of the incised part of this opening 103a sharp and an inner blade 105 rotatably fitted in the above mentioned outer blade 104 and formed by incising a part of the side surface on the tip side rotated inside the above mentioned outer blade 104 and making the edge part of the incised part sharp. The above mentioned outer blade 104 and inner blade 105 are made, for example, of cylindrical stainless steel or the like and are meshed with each other to be able to resect a tissue within a body cavity.

The above mentioned outer blade 104 on the base side is engaged with and fixed to a fixing member 106 which is fitted in a fitting member 107 screwed and fixed to a screw part on the front end side of the above mentioned body 102 and is secured, for example, by soldering or brazing. On the other hand, the above mentioned inner blade 105 on the base side is engaged with and fixed to a connecting member 108 which is removably connected with a connecting member 110 fixed to a rotary shaft of a motor 109 fitted in the above mentioned body 102.

A suction hole 111 communicating with a cavity 112 formed by the above mentioned fitting member 107 and body 102 is provided in the above mentioned connecting member 108 and communicates with an opening 103a of the above mentioned outer blade 104 through the cylindrical interior of the above mentioned inner blade 105. Further, the above mentioned cavity 112 communicates with a suction joint 114 provided at the rear end of the above mentioned body 102 through a suction path 113 which consists, for example, of an inclined path part opening in the above mentioned cavity 112 and a path part passing in the axial direction through the body 102 and to which further the above mentioned suction joint 114 and a sucker not illustrated are connected by a suction tube 115.

On the other hand, a power source cord 116 is soldered to the motor 109 fitted in the above mentioned body 102, is pulled out of a lid 117 at the rear end of a housing part of the above mentioned motor 109 and is connected with a control box not illustrated to feed electricity to the above mentioned motor 109.

Here, a sucked amount adjusting valve 118 is provided in the inclined path part of the above mentioned suction path 113 and is formed of a piston 119 slidably fitted in a cylinder hole provided in the above mentioned body 102 in the direction vertical to the above mentioned suction path 113 and a suction adjusting hole 120 provided in this piston 119 which projects in the end part as a valve operating part 119b out of the above mentioned body 102 as shown in FIG. 30(a). Further, the above mentioned piston 119 has peripheral grooves formed on the outer peripheral surface with the above mentioned suction adjusting hole 120 between them. O-rings 121 made, for example, of silicon rubber are fitted respectively in these peripheral grooves and are contacted with a cylinder hole provided in the above mentioned body 102 to have a sealing function for the outer part.

By the above mentioned formation, for example, in the case of resecting a semicircular plate part of a knee joint or the like, the insertable part 103 of the surgical resecting instrument 101 is inserted into a stinging hole formed in the knee joint, the motor 109 fitted in the above mentioned body 102 is driven and the inner blade 105 fitted in the outer blade 104 of the above mentioned insertable part 103 is rotated through the connecting member 108 from the connecting member 110 fixed to the rotary shaft of this motor 109.

By the rotation of this inner blade 105, the tissue part entering the inside of this outer blade 104 from the part on which the above mentioned outer blade 104 is pressed is resected by the rotated inner blade 105. The resected tissue pieces and irrigating water pass through the cylindrical interior of the above mentioned inner blade 105 from the opening 103a of the tip of the above mentioned insertable part 103, come to the cavity 112 through the suction hole 111 provided in the connecting member 108 and are sucked and discharged out of the body by the sucker not illustrated through the suction path 113. At this time, the sucked amount of the resected tissue pieces and irrigating water is adjusted by the sucked amount adjusting valve 118 provided in the above mentioned suction path 113 while the operation progresses.

In the above mentioned sucked amount adjusting valve 118, when the valve operating part 119b projected out of the above mentioned body 102 is pushed to slide the piston 119, the open area of the path formed of the suction adjusting hole 120 provided in the above mentioned piston 119 and the above mentioned suction path 113 will be able to be continuously varied from zero to the cross-sectional area of the above mentioned suction path 113 at the maximum and the path area will be adjusted.

Figure 35A:
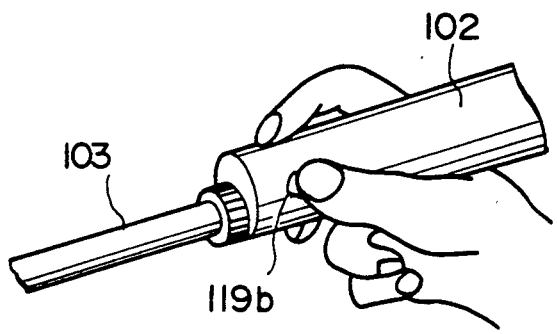
Figure 35B:
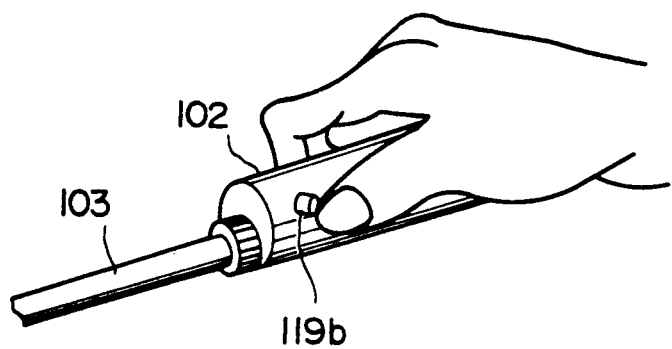

Therefore, in the case that the body 102 of the surgical resecting instrument 101 is held as shown, for example, in FIGS. 35(a) and 35(b) or in any other holding way, without using both hands, the valve operating part 119b will be pushed with one hand to slide the piston 119 and the sucked amount of the irrigating water or resected tissue will be easily adjusted by the sucked amount adjusting valve 118. That is to say, when the valve operating part 119b of the sucked amount adjusting valve 118 provided in the above mentioned body 102 is projected on the side of the above mentioned body 102 and is pushed with a finger, the path area of the above mentioned suction path 113 will be adjusted, the operation will be easy and the resected tissue will be quickly sucked and will be able to be discharged out without clogging.

Now, the sucked amount adjusting valve 118 in FIG. 31 shall be explained. FIG. 31 is the same as FIG. 30 except that the formation of the sucked amount adjusting valve 118 is different. The same parts shall not be explained here.

A piston 119 comprises a large diameter part 119a having a suction adjusting hole 120 and a small diameter part 119b which is a valve operating part, is fitted vertically to the suction path 113 of the body 102 of the surgical resecting instrument 101 and has this small diameter part 119b projected out of the above mentioned body 102. A set screw 122 screwed with a screw part provided on the end part side of the above mentioned large diameter part 119a is fitted to the body 102 fitted with the piston 119. A spring 123 is interposed between this set screw 122 and the end part of the large diameter part 119a of the above mentioned piston 119 to energize the above mentioned piston 119. Further, the above mentioned piston 119 has peripheral grooves formed on the outer peripheral surface with the above mentioned suction adjusting hole 120 between them. O-rings 121 made, for example, of silicon rubber are fitted respectively in these peripheral grooves.

Here, when the valve operating part 119b of the above mentioned sucked amount adjusting valve 118 is not pressed, the suction path of the above mentioned body 102 and the suction adjusting hole 120 of the above mentioned piston 119 will coincide with each other and, when the above mentioned valve operating part 119b is pushed and slid with a finger, the open area of the path formed of the above mentioned suction adjusting hole 120 and the above mentioned suction path 113 will be able to be continuously made small and likewise the sucked amount of the irrigating water and resected tissue will be adjusted. At this time, as the above mentioned piston 119 is energized by the spring 123, if the finger is released, the original state will return, the sucked amount will be able to be adjusted by the force pressing and holding the valve operating part 119b of the above mentioned sucked amount adjusting valve 118 and the operatability will be high.

By the way, the other formations are the same as in FIG. 30 and the operations are the same.

By the way, the pressing force for the above mentioned piston 119 adjusting the sucked amount can be controlled by adjusting the above mentioned set screw 122.

Now, the sucked amount adjusting valve 118 in FIG. 32 shall be explained. In FIG. 32, when the valve operating part 119b of the above mentioned piston 119 is not pressed, the sucked amount adjusting hole 120 of the piston 119 in FIG. 31 will not coincide with the suction path 113 of the above mentioned body 102 and the above mentioned piston 119 will intercept the suction path 113. Therefore, when the valve operating part 119b of the above mentioned piston 119 is pressed and slid with a finger, the open area of the path formed of the above mentioned suction adjusting hole 120 and suction path 113 will be able to be gradually made larger from the intercepted state contrary to FIG. 31 and the sucked amount will be adjusted.

Now, the sucked amounnt adjusting valve 118 in FIG. 33 shall be explained. FIG. 33 is the same as FIGS. 20, 31 and 32 except that the formation of the sucked amount adjusting valve 18 is different. The suction path 113 provided in the body 102 of the surgical resecting instrument 101 is formed of the inside diameter of an elastic tube 122 made, for example, of a silicon tube. On the other hand, in the above mentioned body 102, a slider 124 is slidably provided vertically to the axial direction of the above mentioned elastic tube 122 and forms the above mentioned sucked amount adjusting valve 118.

The above mentioned slider 124 has a flange part 124a substantially in the middle. On one side of this flange part 124a, a cylindrical valve operating part 124b projects out of the above mentioned body 102. On the other side of the flange part 124a, a cylindrical rod 124c is opposed at the tip to the above mentioned elastic tube 122. The tip of this rod 124c is formed to be smooth and spherical and is finished so as not to hurt or damage the above mentioned elastic tube 122. The above mentioned slider 124 is energized by a spring 123 from the rod 124c side through the flange part 124a so that, when the above mentioned operating part 124b is not pressed, the spherical tip of the above mentioned rod 124c may contact the outer periphery of the above mentioned elastic tube 122 part so slightly as not to deform the above mentioned elastic tube 122.

By the above mentioned formation, when the valve operating part 124b of the slider 124 is pressed with a finger, the spherical tip of the rod 124c of the above mentioned slider 124 will press and deform the above mentioned elastic tube 122, the open area of the suction path 113 will be reduced and the sucked amount of the irrigating water and resected tissue will be adjusted. In such case, the same operation and effect as in FIGS. 31 and 32 will be obtained. In FIG. 33, as the above mentioned suction path 113 is formed of the above mentioned elastic tube 122, the O-rings 121 for the outside sealing will not be required. Therefore, the energizing force of the spring 123 can be set to be weaker by the sliding resistance of these O-rings 121, the sucked amount can be adjusted with a lighter operating force and the operatability will further improve.

By the way, in order to prevent the rotation of the above mentioned piston 119 and slider 124, the sucked amount adjusting valve 118 may not be circular but may be polygonal in the cross-section or may be provided with a rotation preventing pin. Also, as shown in FIG. 34, an eccentric column may be combined to make a piston 125. Further, the valve operating part 119b of the above mentioned piston 119 and the valve operating part 124b of the slider 124 may be marked with a color or character to elevate the visibility and to make the opening and closing of the suction path 113 easy to see.

A sucked amount adjusting valve 118 in FIG. 36 shall be explained in the following. FIG. 36 is of the same formation as of the sucked amount adjusting valve in FIG. 30 except having a clicking mechanism.

A piston 119 forming the sucked amount adjusting valve 118 is provided on the peripheral wall with recesses 130a and 130b. A pin 132 pressed by a spring 131 is engaged with either one of these recesses 130a and 130b so that the piston 119 may not move in the lengthwise direction. For example, if the pin 132 engages with the recess 130a, the sucked amount adjusting hole 120 and suction path 113 will communicate with each other and, if the pin 132 engages with the recess 130b, the suction path 113 will be intercepted. In order to release the sucked amount adjusting valve 118 from such communicating state or intercepted state as is mentioned above, the piston 119 is strongly pushed in to push up the pin 132 against the spring 131 and to release the engaging state.

By the way, the sucked amount adjusting hole 121 may be substantially elliptic as in FIG. 38(a), may be of a partly incised circle as in FIG. 38(b), may be triangular as in FIG. 38(c) and further may be of any other shape.

In the above mentioned respective embodiments, it is not described to wash the suction path. The washing may be made easy by such formation as in FIGS. 39 to 44.

In FIG. 39, an insertable part 153 comprises a rigid elongate outer tube 161 and an inner tube 171 rotatably fitted in this outer tube 161. The above mentioned outer tube 161 has an outer pipe 163. An outer blade 165 provided with a cutting blade 164 in the edge part of a semicircular opening is fitted to the tip part of this outer pipe 163 and is fixed by soldering or the like. A flange 166 removably connectable with the above mentioned body 152 is fitted to the base end part of the above mentioned outer pipe 163 and is fixed by soldering or the like.

The above mentioned inner tube 171 has an inner pipe 173 insertable into the above mentioned outer pipe 163. An inner blade 175 provided with a cutting blade 174 in the edge part of a semicircular opening is fitted to the tip part of this inner pipe 173 and is fixed by soldering or the like. A sleeve 176 engaged with the output shaft of a motor within the above mentioned body 152 and is fixed by soldering or the like. By the way, the above mentioned inner blade 175 is arranged within the above mentioned outer blade 165.

A suction path 181 is formed within the above mentioned inner pipe 173. Near the tip of the above mentioned insertable part 153, an opening 182 for taking in tissues communicating with the above mentioned suction path 181 is formed of a semicircular opening of the above mentioned inner blade 175 and outer blade 165. The above mentioned sleeve 176 is provided with a suction hole 183 communicating with the above mentioned suction path 181 and provided vertically to the axis of the above mentioned inner pipe 173 and a washing hole 185 for washing the suction path communicating with the above mentioned suction path 181 and formed substantially coaxially with this suction path 181.

Now, the operation shall be explained.

For example, in the case of resecting an object part within a knee joint cavity, a small hole for inserting the insertable part 153 of the surgical resecting instrument 151 is formed in the knee part with a trocar or the like and the above mentioned insertable part 153 is inserted into this small hole through a trocar or the like or directly. While the joint cavity interior is being observed with a joint scope inserted into the joint cavity through a trocar or the like, the opening 182 near the tip of the above mentioned insertable part 153 is contacted with the resected object tissue and, in this state, the motor within the body 152 is driven to rotate the inner tube 171 through the sleeve 176. When the above mentioned inner tube is rotated, the tissue will be resected by the cutting blade 164 of the outer blade 165 and the cutting blade 174 of the inner blade 175 and the resected pieces will be sucked and discharged by the sucking apparatus 7 through the opening 182, suction path 181, suction hole 183 and suction tube 8.

On the other hand, in the case of washing the suction path 181 within the inner tube 171 of the surgical resecting instrument 151, for example, as shown in FIG. 40, a washing brush 186 is inserted into the suction path 181 through a washing hole 185 formed in the sleeve 176 and the suction path 181 is cleanly washed to the opening 182 at the tip with this washing brush 186 By the way, in the case of washing the inner tube 171, this inner tube 171 is pulled out of the outer tube 161.

On the other hand, as shown in FIG. 44, if the above mentioned washing hole 185 is not made, it will be very difficult to insert the washing brush 186 into the suction path 181.

Thus, according to the above mentioned embodiment, as the washing hole 185 communicating with the suction path 181 is provided substantially coaxially with the suction path 181, the clogging of the suction path 181 within the inner tube 171 can be easily and positively removed and washed and the surgical resecting instrument 151 can be always kept clean.

Now, FIG. 41 shall be explained. The shape of the tip of an inner blade 195 is different from the shape of the inner blade 175. That is to say, in the tip part of the above mentioned inner blade 195, a washing hole 196 is provided substantially coaxially with the suction path 181.

According to the formation in FIG. 41, for example, in the case of removing the clogging of the suction path 181, if a fine rod is inserted through either of the washing holes 185 and 196 and the clogging tissue is pushed out to the other washing hole, the clogging will be able to be easily removed.

The other formations, operations and effects are the same as in FIG. 39.

FIG. 42 shall be explained in the following. In FIG. 42, the same as in FIG. 41, the washing hole 196 is provided substantially coaxially with the suction path 181 in the tip part of the inner blade 195 and the washing hole 185 is provided in the sleeve 176.

In this embodiment, the washing brush 186 or the like is inserted through the washing hole 196 provided in the above mentioned inner blade 195 and the suction path 181 can be washed.

The other formations, operations and effects are the same as in FIG. 39.

Now, FIG. 43 shall be explained. FIG. 43 is of an example of a surgical resecting instrument having a spherical cutting blade for forming cartilages.

In FIG. 43, the outer blade 165 is opened on the tip side and is incised on the side. In the rear of this incision 201, a plurality of tissue suction holes 202 are provided in the peripheral direction.

On the other hand, in the tip part of the inner pipe 173, a spherical cutting blade 205 is fitted through a connecting part 204 and projects out of the opening at the tip of the above mentioned outer blade 165 and the incision 201 on the side. A tissue suction hole 206 is provided on the tip side of the above mentioned inner pipe 173 and in the position rearward from the tissue suction hole 202 formed in the above mentioned outer blade 165.

By the way, the same as in FIG. 39, the sleeve 176 is fitted to the base end part of the above mentioned inner pipe 165 and is provided with the suction hole 183 and washing hole 185.

In the surgical resecting instrument in FIG. 43, when the spherical cutting blade 205 is contacted with a tissue and is rotated through the inner pipe 173, the tissue will be resected. The resected piece 208 resected by the above mentioned spherical cutting blade 205 will be sucked into the suction path 181 within the inner pipe 173 through the tissue suction hole 202 of the outer blade 165 and the tissue suction hole 206 of the inner pipe 173 and will be discharged out of the body.

The other formations, operations and effects are the same as in FIG. 39.

By the way, as shown in FIGS. 45 to 48, in the case of resecting a living body tissue, a member holding this tissue may be provided in the insertable part.

In FIG. 45, an insertable part 213 comprises an outer blade 216 fixed in the opened base part to the tip part of the body 212 and an inner blade 217 internally fitted rotatably around the axis within this outer blade 216 which is made, for example, of cylindrical stainless steel and is formed of a pair of incised blade parts 218 extending in the lengthwise direction through a tissue intake port opened at the tip. On the respective longitudinally extending edges of this pair of incised blade parts 218, serrated cutting blades 219 having pointed parts at the tips are formed as tissue holding members. On the other hand, the inner blade 217 is made, for example, of stainless steel or the like and has at the tip two boring cutting blades 220 boring cutting in the axial direction formed to be V-shaped as opposed in the diametral direction and on the outer periphery a horizontally cutting screwlike cutting blade 221 formed.

By the above mentioned formation, a tissue is taken in with the pair of incising blade parts 218 of the above mentioned outer blade 216 and the above mentioned inner blade 217 is rotated by a motor internally fitted in the above mentioned body 212 to cut and resect the tissue. The resected piece is sucked and discharged by the cut piece sucking apparatus 7 through the suction tube 8 fitted to the above mentioned body 212.

In the case of using the thus formed surgical resecting instrument to partly resect, for example, a semicircular plate of a knee joint within the body cavity, as shown in FIGS. 46(a) and 46(b), the semicircular plate 222 is taken in between a pair of incising blade parts 218 of the outer blade 216 of the above mentioned insertable part 213 and, in this state, the inner blade 217 internally fitted in the insertable part 213 is rotated.

At this time, the above mentioned semicircular plate 222 will be held between the above mentioned pair of incised blade parts 218 by the pointed parts at the tips of the serrated cutting blades 219 provided on the above mentioned pair of incised blades 218 to prevent the cut tissue from escaping due to the cutting pressure in the case of boring cutting and horizontal cutting by rotating the above mentioned inner blade 217. Therefore, the above mentioned semicircular plate 222 can be positively taken in by the outer blade 216 and the tissue to be cut can be positively cut and resected.

The resected tissue piece is recovered by the cut piece sucking apparatus 7 through the suction tube 8.

Now, FIG. 5 shall be explained.

FIG. 47 is the same as FIG. 46 except that the inner blade 217 is different in the shape and formation. In this inner blade 217a, a cutter blade 223 made of stainless steel or the like is engaged with and fixed to the tip through a hollow shaft 224 made of stainless steel or the like and transmitting a power from the body 3. In this cutter blade 223, two boring cutting blades 220a boring cutting in the axial direction are formed to be V-shaped as opposed in the diametral direction at the tip and a cutting blade 225 for horizontal cutting is formed on the outer periphery. The above mentioned cutter blade 223 is provided with a suction hole 226 sucking and discharging resected pieces.

By the above mentioned formation, the same as in FIG. 45, the tissue to be cut is held between the pair of incised blade parts 218 of the outer blade 216 and the resected piece bored cut and horizontally cut by the inner blade 217a is sucked through the suction hole 226 provided in the above mentioned cutter blade 223, is fed to the body 3 of the surgical resecting instrument 1 through the hollow shaft 224 and is sucked and discharged by the cut piece sucking apparatus 7 through the suction tube 8 fitted to the body 3. That is to say, in the case of cutting and resecting the tissue to be cut, the escape of the tissue will be prevented and the tissue will be positively resected.

FIG. 48 shall be explained in the following.

FIG. 48 is the same as FIGS. 45 and 47 except that the outer blade 216 is different in the shape and formation. This outer blade 216a is made, for example, of cylindrical stainless steel or the like and is provided at the tip with a pair of incised blade parts 218a extending in the lengthwise direction. A pair of projections 227 are provided at the tips of this pair of incised blade parts 218a. Further, cutting blades 228 extending in the axial direction are formed in the edge parts of this pair of incised blade parts 218a.

By the above mentioned formation, for example, in the case of resecting a semicircular plate part of a knee joint, the semicircular plate 222 taken in between the pair of incised blade parts 218a will be held by the pair of projections 227 provided at the tips of this pair of incised blade parts 218a. Therefore, in the same manner, the escape of the cut tissue by the cutting pressure will be prevented and the tissue will be positively resected.

By the way, the materials and shapes of the outer blades 6 and 6a and inner blades 7 and 7a are not limited to those described above but may be variously set and formed.

For example, the material is not limited to stainless steel but may be such material available for blades as super steel or ceramics. The boring cutting blades 220 and 220a provided in the tip parts of the inner blades 217 and 217a and formed to be V-shaped need not be opposed in the diametral direction and need not be limited to be two but may be three or more. The number and pitch of the serrations of the serrated cuttting blades 219 provided on the pair of incised blade parts 218 of the above mentioned outer blade 216 are not limited to those of the embodiment. For example, the serrated blade may be provided only on one side of the above mentioned pair of incised blade parts 218. Further, the edges of the above mentioned pair of incised blade parts 218 and 218a need not be cutting blades but may be, for example, rough surfaces or pearskin finishes to hold tissues.

As explained above, according to the present invention, as the shearing angle formed by the shearing blade part and the blade part of the outer blade is formed to vary with the shearing process, the quick increase of the shearing power can be prevented, the safety is high, the cost is low and the cutting efficiency is high.

What is claimed is:

1. A surgical resecting instrument comprising:

a body part having a rotary driving means;

an insertable part adapted to be inserted into a tissue within a living body attached to and extending away from a front end part of said body part, said insertable part including a tubular outer member forming an outer shell of said insertable part and an inner tube provided internally of said tubular outer member and rotated and driven by said rotary driving means, said tubular outer member having an open tip part, said inner tube having a center of a tip surface which is V-shaped with an apex of said V-shaped tip surface extending toward a rear of said inner tube;

an outer blade of tubular form provided in said open tip part of said tubular outer member, said outer member having a slot in a sidewall thereof extending from said tip of said outer member toward said body part and said outer blade having a blade part formed at an edge of said slot;

an inner blade provided at a tip part of said inner tube within said outer blade for shearing a living body tissue together with said blade part of said outer blade, said inner blade having a shearing blade part formed so that an angle formed with said blade part of said outer blade, at the beginning of a shearing action, will be larger than the angle formed with said blade part of said outer blade as said shearing action continues and at least one of said shearing blade part of said inner blade and said blade part of said outer blade is formed as a circular arc.

2. A surgical resecting instrument according to claim 1 wherein said blade part is formed to be linear in the lengthwise direction of said outer tube.

3. A surgical resecting instrument according to claim 2 wherein said shearing blade part is formed to be arcuate so that the angle formed by said blade part and shearing blade part in the course of the shearing may be smaller than the angle formed by said blade part and shearing blade part at the beginning of the shearing.

4. A surgical resecting instrument according to claim 2 wherein said shearing blade part is cut with a columnar cutting tool.

5. A surgical resecting instrument according to claim 1 wherein said shearing blade part is formed to be linear in the lengthwise direction of the inner tube.

6. A surgical resecting instrument according to claim 5 wherein said blade part is formed to be arcuate so that the angle formed by said shearing blade part and blade part in the course of the shearing may become gradually smaller than the angle formed by said shearing blade part and blade part at the beginning of the shearing.

7. A surgical resecting instrument according to claim 1 wherein said inner blade has a window for sucking the resected living body tissue.

* * * * *